United States Patent
Allegretti et al.

(10) Patent No.: US 12,186,544 B2
(45) Date of Patent: Jan. 7, 2025

(54) INJECTION ASSEMBLY WITH MOVABLE SLEEVE

(71) Applicant: Becton, Dickinson and Company, Franklin Lakes, NJ (US)

(72) Inventors: Andrew Allegretti, Nyack, NY (US); Peter Girgis, East Brunswick, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 318 days.

(21) Appl. No.: 17/599,477

(22) PCT Filed: Mar. 20, 2020

(86) PCT No.: PCT/US2020/023820
§ 371 (c)(1),
(2) Date: Sep. 28, 2021

(87) PCT Pub. No.: WO2020/205275
PCT Pub. Date: Oct. 8, 2020

(65) Prior Publication Data
US 2022/0176045 A1   Jun. 9, 2022

Related U.S. Application Data

(60) Provisional application No. 62/826,225, filed on Mar. 29, 2019.

(51) Int. Cl.
*A61M 5/32* (2006.01)
*A61M 5/34* (2006.01)
*A61M 5/46* (2006.01)

(52) U.S. Cl.
CPC .......... *A61M 5/326* (2013.01); *A61M 5/3245* (2013.01); *A61M 5/3286* (2013.01);
(Continued)

(58) Field of Classification Search
CPC .. A61M 5/178; A61M 5/3129; A61M 5/3202; A61M 5/3245; A61M 5/321
See application file for complete search history.

(56) References Cited

U.S. PATENT DOCUMENTS

| 5,246,428 A | 9/1993 | Falknor |
| 2002/0169421 A1 | 11/2002 | McWethy et al. |

(Continued)

FOREIGN PATENT DOCUMENTS

| CN | 1635919 A | 7/2005 |
| CN | 102470219 A | 5/2012 |

(Continued)

OTHER PUBLICATIONS

International Search Report dated Jun. 16, 2020, which issued in the corresponding PCT Patent Application PCT/US2020/023820.

*Primary Examiner* — Tiffany Legette
(74) *Attorney, Agent, or Firm* — Dickinson Wright PLLC

(57) ABSTRACT

An injection assembly includes a syringe barrel (12) having a proximal end and a distal end, a needle hub (20) supporting the needle and coupled to the distal end of the syringe barrel (12). A sleeve (32) is positioned on the syringe barrel and needle hub for sliding between a first position where the needle is covered and a second position exposing the needle. The sleeve (32) is biased to the extended position to cover the needle. The sleeve has a distal end (38) and a proximal end (40). During use, the syringe is positioned against the skin of the patient so that distal end of the sleeve contacts the skin of the patient before the needle so that lateral or angular force applied relative to the surface of the skin is absorbed by the sleeve to inhibit sliding of the sleeve and resist bending of the needle during insertion.

13 Claims, 12 Drawing Sheets

(52) U.S. Cl.
CPC .......... *A61M 5/3293* (2013.01); *A61M 5/345* (2013.01); *A61M 5/46* (2013.01); *A61M 2005/3267* (2013.01)

(56) References Cited

U.S. PATENT DOCUMENTS

| | | |
|---|---|---|
| 2005/0113750 A1 | 5/2005 | Targell |
| 2013/0226085 A1 | 8/2013 | Roberts et al. |
| 2014/0243755 A1 | 8/2014 | Slemmen et al. |
| 2017/0165429 A1* | 6/2017 | Holmqvist ............ A61M 5/326 |

FOREIGN PATENT DOCUMENTS

| | | | |
|---|---|---|---|
| CN | 104968384 A | 1/2015 | |
| CN | 212662386 U | 3/2021 | |
| EP | 2742963 A1 | 6/2014 | |
| JP | 2004-533282 A | 11/2004 | |
| JP | 2013-500745 A | 1/2013 | |
| JP | 2015-536772 A | 12/2015 | |
| WO | WO-9909898 A1 * | 3/1999 | ......... A61B 17/3211 |
| WO | 2017-170502 A1 | 10/2017 | |

* cited by examiner

INJECTION ASSEMBLY WITH MOVABLE SLEEVE

This application claims priority to U.S. provisional patent application Ser. No. 62/826,225 filed on Mar. 29, 2019, which is hereby incorporated by reference in its entirety.

FIELD OF THE INVENTION

An injection assembly or a delivery assembly, such as a syringe assembly, has a movable sleeve that can be retracted during use. The assembly also has a movable member sleeve around the needle for assisting in guiding the needle during use and minimizing bending of the needle.

DESCRIPTION OF THE RELATED ART

Needle lengths in the range of 4 mm to 5 mm can be difficult to insert into a patient when the needle is not perpendicular to the surface of the skin. The short length requires the needle to pierce the skin in a straight line to ensure proper penetration and reduced the risk of the needle bending.

The insertion of a needle into the skin of a patient is determined primarily by the features of the needle and not the features or structure of the needle support as disclosed in Needle Insertion Modeling; Identifiability and Limitations, L. Barbe, *Biomedical Signal Processing and Control* 2 (207) 191-198. Needle insertion into the skin of patient is generally classified into three phases that influence the injection depth. The first phase corresponds to the initial contact of the needle with the skin where the tissue deforms without puncturing the surface of the skin. A second phase refers to the puncture of the skin and the relaxation of the skin when the insertion force of the needle is stopped. The third phase is where the needle is extracted and pulls or stretches the skin outward as the needle is extracted.

Needle lengths, such as needles having a length of about 4 mm to 5 mm are adapted to inject a medication to a specified target depth in a subcutaneous region. The present invention provides a structure so that a needle can be consistently inserted to a desired target depth. Prior pen needles have the cannula supported on an axial post extending from the hub. The post forms a narrow portion and a relatively wider base that does not contact the skin during the injection. In other pen needles known in the art, a distal face of the hub placed against the injection site may be relatively large, and may be provided with a slight taper at the edge. The edge of the hub can engage the skin when the cannula is inserted at an angle relative to the surface of the skin of the patient.

Various injection devices have been produced where the supporting structure does not contact the skin during injection or extraction of the needle. Other devices have been proposed where the end face of the device is positioned to contact the surface of the skin to limit the depth of penetration into the patient.

Pen-injector delivery devices facilitate self-administration of parenteral medications. Pen needles are a component of needle-based injection systems and consist of a doubled ended cannula assembled into a plastic hub using adhesive. The hub has internal threads, which allow it to be attached to the pen-injector device. Pen needle attachment allows the proximal end of cannula to penetrate through the rubber septum of the medicament cartridge to create the fluid flow path. For many diabetics maintaining blood glucose control is achieved by performing multiple daily injections of insulin into the subcutaneous (SC) tissue using pen injector delivery devices developed to be a convenient, discreet alternative to the vial and syringe. Numerous pen injectors are commercially available in either disposable or multi-use configurations, each offering various patient-centric features. The distal pen needle cannula interfaces with the delivery site providing a conduit for delivery. Pen needle designs are intended to enable consistent delivery to the target tissue space, minimize leakage of injectate, and reduce pain/discomfort and site effects such as bleeding and bruising associated with the injection. The primary design features, needle length/gauge and hub face geometry, in conjunction with mechanics of the delivery system and injection technique, dictate injection success.

Injections may be performed in the intradermal region, the subcutaneous region and the intramuscular (IM) region of the skin. For many types of injectable medications, including insulin, the SC region is preferred for administering an injection. See, for example, Lo Presti, et al., Skin and Subcutaneous thickness at injecting sites in children with diabetes: ultrasound findings and recommendations for giving injection, *Pediatric Diabetes* (2012).

While the prior devices are generally suitable for the intended use, there is a continuing need for improved devices for controlling the depth of penetration of a cannula for delivering a drug or medicament to a selected target area.

SUMMARY

The disclosure describes a delivery assembly and an injection assembly, such as a syringe assembly, to assist in introducing the needle into the patient at a controlled angle and position. In one embodiment, the syringe assembly provides the needle with a retractable sleeve or shield that is movable between a first position extending distally from the needle tip and a second retracted position for injecting the substance to a desire depth into the patient.

The syringe assembly in one embodiment includes a syringe barrel having a proximal end for receiving a plunger and a distal end with a needle. A movable sleeve is coupled to the distal end of the syringe that can slide between an extended position where the needle is covered by the sleeve and a retracted position where the needle is exposed. The sleeve can be biased toward the distal end and can be moved to the retracted position by contact with the skin of the patient during insertion of the needle into the patient.

In one embodiment, the assembly includes a syringe with a distal end supporting a cannula and an adapter coupled to the distal end of the syringe. The adapter can be a separate member that is fixed to the syringe barrel or removable from the syringe barrel. The adapter has a body that fits on the distal end of the syringe, a movable shield that slides on the body of the adapter, and a biasing member, such as a spring. In one embodiment, the shield is continuously biased in the distal direction relative to the adapter without a mechanical latch or lock mechanism that would prevent sliding of the shield on the body of the adapter.

The body of the adapter has a substantially cylindrical wall with an open proximal end configured for coupling with the distal end of the syringe and an open distal end with a dimension where the distal end of the syringe is able to project from the body. The outer surface of the body has a track, a stop member at the proximal end of the body, and stop at the distal end of the body. A spring surround the body and has a proximal end engaging the proximal stop member of the body. A shield has a guide member that slides in the track of the body and a stop member extending radially outward at the proximal end of the shield. The stop member is configured to contact the distal end of the spring.

In one embodiment, the movable sleeve is spring biased toward the distal end of the syringe. A flange or collar is coupled to the syringe barrel. The sleeve is mounted on the distal end of the syringe for sliding movement relative to the syringe and the needle. A spring is positioned between the collar and a proximal end of the sleeve to bias the sleeve in the distal direction. The distal end of the sleeve contacts the skin of the patient and moves to the retracted position by the insertion force while the needle penetrates the skin. The contact of the sleeve with the patient provides sufficient friction against the patient to inhibit lateral movement of the syringe assembly and needle with respect to the skin surface caused by the insertion force.

In another embodiment, the syringe assembly includes a syringe barrel with a sleeve attached to a distal end of the syringe, where the sleeve slides to a retracted position where the distal end of the syringe is able to contact the surface of the skin during the insertion of the needle into the skin of the patient. In another embodiment, the sleeve is able to retract to a position where the distal end of the syringe projects from the open end of the sleeve to contact and deform the surface of the skin during the penetration of the needle into the patient.

In one embodiment, a method of introducing a substance into the patient is provided by a syringe barrel having a proximal end and a distal end with a needle extending from the distal end. A sleeve is coupled to the syringe barrel and movable from an extended position covering the end of the needle to a retracted position relative to the needle. The syringe barrel and needle can be oriented at an inclined angle relative to the surface of the skin of the patient such that during the penetration of the needle into the skin, the sleeve contacts the surface of the skin before the tip of the needle contacts the skin. The sleeve remains in contact with the skin during insertion of the needle into the skin of the patient to resist lateral forces between the needle and the surface of the skin to inhibit bending of the needle by a lateral force relative to the skin. The sleeve is retracted by the insertion force until the distal end of the syringe engages the surface of the skin to limit the depth of penetration of the needle. The sleeve is biased to the extended position when the needle is withdrawn from the skin.

In one embodiment, a syringe is provide with a sleeve that slides between an extended position and a retracted position on the tip of the syringe to cover the need when not in use and retract during the penetration of the needle into the skin of the patient. The sleeve has a body surrounding the syringe barrel and an end wall with an opening to allow the needle to extend from the sleeve when the sleeve is retracted.

In another embodiment, the injection assembly is a pen needle formed with a sleeve to cover the needle and move between an extended position and a retracted position. The pen needle is configured to be attached to a delivery device, such as a standard pen needle delivery device. The pen needle includes a body having a side wall with an open proximal end and a closed distal end. A needle extends from the distal end for piercing the skin of the patient for injecting a medication into the patient. The sleeve is coupled to the pen needle for sliding movement on the outer surface of the side wall. A biasing member, such as a spring, is provided between the side wall of the pen needle and the moveable sleeve to bias the sleeve in the distal direction with respect to the body of the pen needle. In one embodiment, the sleeve has an inwardly extending flange at a proximal end that engages an outwardly extending collar on a side wall of the pen needle to limit sliding movement in the proximal direction. A flange is provided at a distal end of the body for engaging the flange on the sleeve to limit sliding movement in the distal direction. A spring is positioned between the distal end of the side wall of the body and a distal end of the sleeve to bias the sleeve in the distal direction.

The features are basically attained by providing an injection device comprising a body connected to a fluid supply, the body having a proximal end and a distal end, a needle hub coupled to said distal end of said body and having a skin contact face. A needle extends from said distal end of the body. The needle has an axial length, a proximal end coupled to the needle hub, and a distal end spaced from the skin contact face. A movable sleeve is provided on the body for sliding movement between an extended position and a retracted position on the body in an axial direction with respect to the body. The sleeve has a proximal end connected to the body and a distal end. The sleeve is biased in the distal direction where the distal end of the sleeve is oriented to cover the distal end of the needle. The sleeve can slide to the retracted position where the distal end of the contact surface of the needle hub is exposed to contact the skin of a patient.

The syringe assembly in another embodiment comprises a syringe barrel having a proximal end and distal end, a tip at a distal end of the syringe barrel forming a skin contact surface, and a needle coupled to the distal end of the syringe barrel. A sleeve is coupled to the syringe barrel for sliding movement on the syringe barrel between an extended position covering the needle, and a retracted position where the skin contact surface distal end of the syringe barrel projects from the sleeve to contact a skin surface of a patient.

A method is provided for introducing a needle into a patient, comprising providing an assembly having body with a proximal end and a distal end forming a skin contact surface. A needle is coupled to the distal end of the barrel. A sleeve is coupled to the barrel for sliding movement between an extended position where the needle is covered and a retracted position exposing the needle. The body and needle are oriented at an incline against the surface of the skin of a patient and an insertion force is applied where the sleeve contacts the surface of the skin before the needle contacts and penetrates the skin to inhibit lateral force of the needle relative to the skin surface.

These and other features of the invention will become apparent from the following detailed description of the invention, which in conjunction with the drawings disclose various embodiments of the invention.

BRIEF DESCRIPTION OF THE DRAWINGS

The following is a brief description of the drawings in which.

DETAILED DESCRIPTION OF THE INVENTION

The delivery assembly or injection assembly refers to a syringe or pen needle having a needle or cannula for injecting a medication or other substance into a patient. The terms needle and cannula are used herein interchangeably to refer to a thin tubular member having a sharp end for insertion into an injection site on a subject. A distal direction is in the direction toward the injection end of the syringe assembly, and the proximal direction is the opposite direction. The axial direction refers to a direction along or parallel to the longitudinal axis of the needle and the needle hub and the radial direction refers to a direction perpendicular to the axial direction.

The intradermal layer in adults generally has a thickness of around 2 to 3 mm, so that intradermal injection depth is in a range of up to about 3 mm as measured from the outer surface of the skin. The thickness of the subcutaneous layer varies depending on the age of the patient, gender, body mass index (BMI), and the part of the body where the injection is administered. The subcutaneous region has an average thickness of about 7 mm to about 15 mm. Insulin is preferably delivered to the subcutaneous region. In the embodiments described herein, the needle or cannula has a suitable length for the intended depth of penetration into the patient. In various embodiments, the needle or cannula has a length of about 4-8 mm. The length of the needle or cannula refers to the exposed length extending from the distal tip of the syringe, pen needle or other delivery device.

The injection assembly is suitable for use in a method for injections and for injecting a drug to a patient. The above description of the preferred embodiments is not to be deemed as limiting. The disclosure is intended to enable the artisan of ordinary skill to practice variants of the assembly described without departing from the scope of the disclosure. Numerical limitations herein, in the specification and in the claims, are understood to be limited by the modifier "about," such that minor departures yielding equivalent results is within the scope of the invention. Features or dependent claim disclosed in connection with one embodiment or independent claim may be combined in another embodiment or with a different independent claim. The features of one embodiment can be used with other embodiments as long as they are not inconsistent with one another.

The delivery device and/or injection assembly is configured for delivering a medication to a patient. In the embodiments described, the injection assembly can be a syringe, pen needle, or similar device that is able to introduce the medication to the patient. The device is configured to assist in the insertion of a needle into a patient with a reduced incidence of bending of the needle caused by misalignment with the skin surface of the patient.

Figure 1:
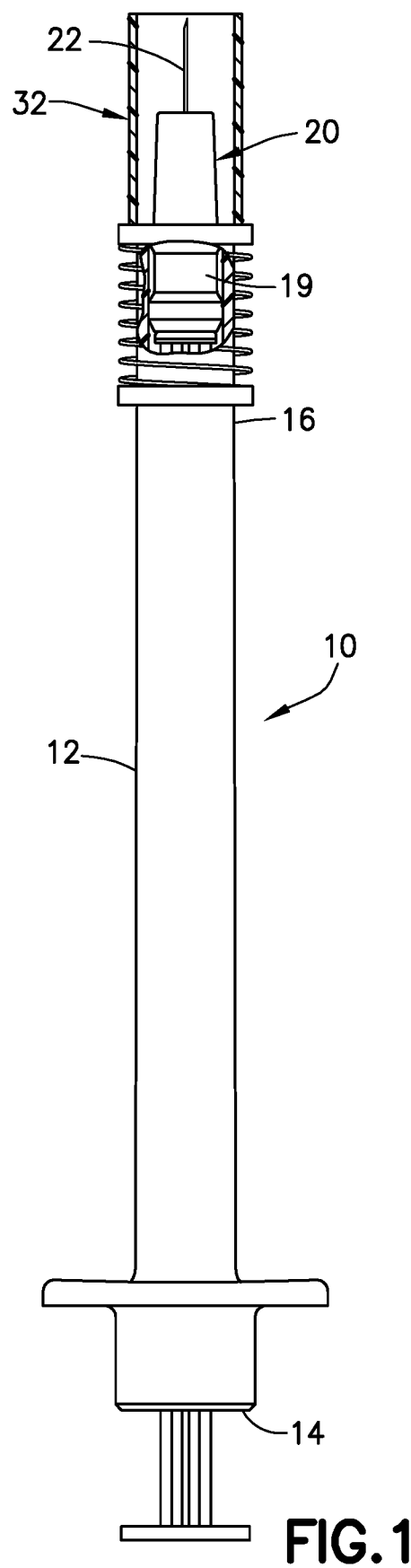
FIG. 1 is a side view of the syringe assembly in one embodiment showing the sleeve in the extended position.

Referring to FIG. 1, the injection assembly in one embodiment is a syringe assembly 10 including a body forming a syringe barrel 12 defining a fluid supply for a medication and having a proximal end 14 and a distal end 16. The proximal end 14 receives a movable plunger rod 18 and stopper 19 for dispensing the substance contained in the syringe assembly.

Figure 2:
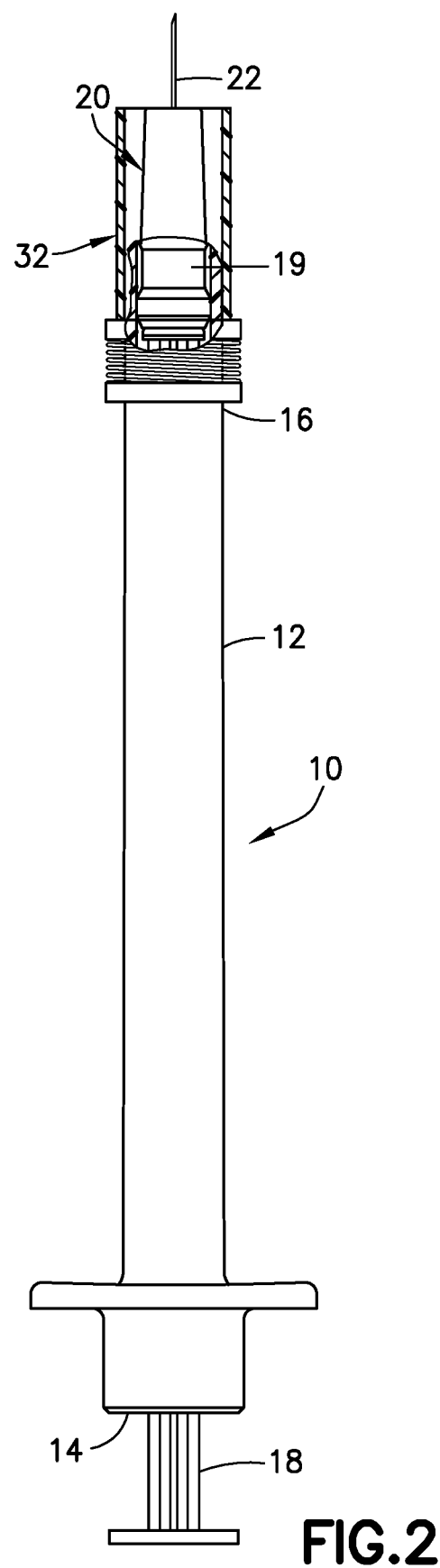
FIG. 2 is a side view of the syringe assembly of FIG. 1 showing the sleeve in the retracted position.

A needle hub 20 is coupled to the distal end 16 of the syringe barrel 12 as shown in FIG. 1 and FIG. 2 providing the fluid supply of the medication. In the embodiment shown, the needle hub 20 is integrally formed with the syringe barrel. The needle hub 20 as shown includes a needle 22 extending axially from the needle hub. The needle hub 20 is oriented at the distal end of the syringe barrel 12 and forms a distal tip of the syringe assembly. The needle hub 20 has a body portion 24 with a proximal end 26 and a distal end 28. In the embodiment shown, the distal end 28 has a distal axial face 30 forming a skin contact surface of the syringe barrel for contacting the surface of the skin of the patient during use. The distal face 30 in the embodiment shown in FIGS. 1 and 2 is substantially flat and oriented in a plane substantially perpendicular to the longitudinal axis of the syringe barrel. The distal end of the needle hub can be formed by a plurality of flanges that extend radially outward and axially to define the substantially flat distal face 30. The distal face 30 of the needle hub 20 is spaced axially from the end of the syringe barrel. In the embodiment shown, the needle hub is fixed to the end of the syringe barrel. In other embodiments, the hub can be separately formed and attached to the syringe barrel. In other embodiments, the distal face and tip of the syringe can have a convex shape to distribute the insertion force over a predetermined surface area to control the shape and depth of the indentation formed in the skin and control the depth of penetration of the needle.

The needle 22 in the embodiment shown has a length of about 4-8 mm extending from the distal face 30 of the body 24 although the exposed length of the needle can vary depending on the particular needs of the syringe apparatus. Needles having an exposed length extending from the distal end of the hub of about 4-6 mm are generally intended to penetrate the skin to a depth for injecting the medication, such an insulin composition. The needle is generally 28 gauge to 32 gauge. In one embodiment, the needle 22 has an exposed length of about 4 mm and can be a 32 gauge needle. In other embodiments, the needle can have a length of 6 mm or more. The needle is intended to penetrate the skin of the patient where the distal face 30 contacts the surface of the skin to limit the depth of penetration. The distal face 30 can have a shape and dimension to assist in deforming and forming an indentation in the surface of the skin in a predetermined configuration to control the depth of penetration of the needle for delivering the medication to the intended depth. In the embodiment shown, the distal face 30 has a flat surface around the needle 22 and a rounded convex outer edge 23 with a diameter of about 3-5 mm for contacting the surface of the skin of the patient.

The syringe assembly 10 includes a mechanism for assisting the needle 22 during penetration to inhibit bending or twisting of the needle relative to the skin when needle is at an inclined angle relative to the surface of the skin. The mechanism contacts the skin before and during the penetration by the needle to reduce the lateral force by the needle with respect to the skin of the patient. Inserting the needle into the skin at an inclined angle can produce a lateral force or sideways force that can cause bending of the needle due to the short length and gauge of the needle.

In the embodiment of FIGS. 1 and 2, the syringe barrel 12 includes a movable sleeve 32 that contacts the skin of the patient during the insertion of the needle into the skin and assists in the penetration with a reduce occurrence of bending the needle when the needle is being inserted at an inclined angle with respect to the surface of the skin. The sleeve 32 is mounted on the syringe barrel for sliding movement between and extended position shown in FIGS. 1 and 3 and a retracted position shown in FIGS. 2, 4, and 5.

Figure 3:
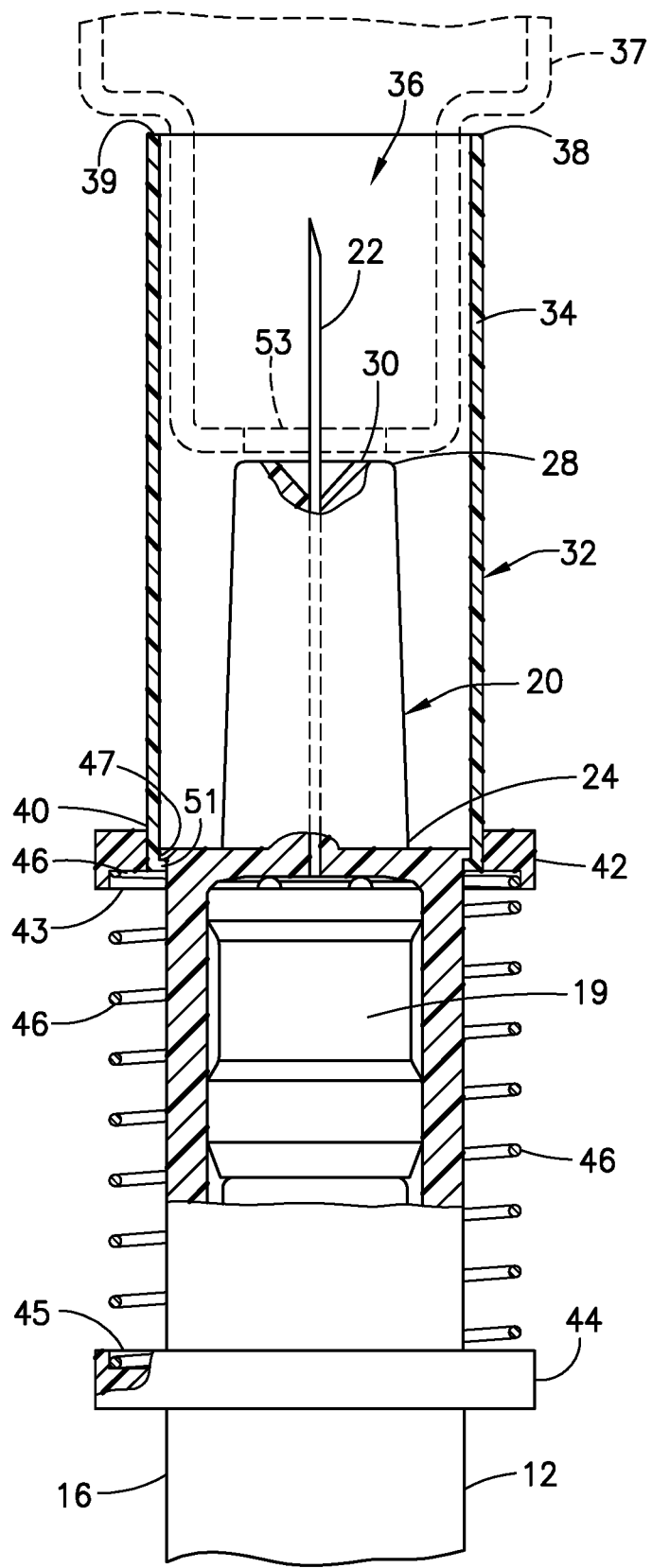
FIG. 3 is an enlarge side view of the syringe tip showing the sleeve in the extended position.

The sleeve 32 in the embodiment shown has a substantially cylindrical shaped side wall 34 having an axial passage 36 with an internal dimension corresponding substantially to the outer dimension of the syringe barrel 12 for sliding movement on the outer surface of the syringe barrel. The sleeve 32 has a cylindrical outer surface and a cylindrical inner surface with an inner dimension corresponding substantially to the outer dimension and outer surface of the syringe barrel 12. The sleeve has open distal end 38 and an open proximal end 40. In the embodiment shown, the sleeve 32 has a longitudinal length complementing the axial length of the hub 20 and the needle 22 and for sliding on the distal end of the syringe barrel. The open distal end 38 of the sleeve 32 has an inner dimension corresponding to the outer dimension of the syringe barrel to slide direction on the syringe barrel. In one embodiment shown in FIG. 3, the open distal end 38 can have a dimension and configuration to assist in aligning the needle with a vial 37 or other container for filling the syringe. As shown in FIG. 3, the open end 38 can have a dimension to receive the neck of the vial 37. In other embodiments, the open end 38 can have a dimension to contact the end of the vial to assist in aligning the needle with a septum 53 on the vial.

In the embodiment shown, the proximal end of the sleeve includes a stop member shown as a flange 42 extending radially outward from the sleeve 32. The flange 42 can be a separate ring shaped member that is coupled to the outer surface of the sleeve 32 by a pressure fit or by bonding to the sleeve by an adhesive, welding or other attachment mechanism. In other embodiments, the ring shaped member can be integrally molded with the sleeve as a one-piece unit. In the embodiment shown, the open distal end 38 of the sleeve 32 has an inner diameter substantially equal to the outer diameter of the syringe barrel to slide over the syringe barrel and the needle hub. The open distal end 38 has an annular shape spaced radially outward from the needle and needle hub to form an annular space between the inner surface of the sleeve and the needle.

In one embodiment, the syringe barrel 12 includes a ring-shaped stop member shown as a collar 44 that is coupled to the outer surface of the syringe barrel proximal the distal end. In the embodiment shown, the collar 44 is fixed to the outer surface of the syringe barrel. The collar 44 can be a separate ring shaped member that is press fitted onto the syringe barrel or attached by an adhesive. In other embodiments, the collar is molded onto the syringe barrel as a one-piece unit. A spring 46 forming a biasing member extends between the sleeve 32 and the collar 44 on the syringe barrel 12 to bias the sleeve in the distal direction to the extended position of FIG. 1. The spring 46 is a coil spring in the embodiment shown that surrounds the outer surface of the syringe barrel and extends between the collar 44 on the syringe and the flange 42 on the sleeve 32. In the embodiment shown, the spring extends between the proximal end of the sleeve 32 and the collar 44 on outer surface of the syringe barrel and the flange 32 so that the spring is not enclosed by the sleeve.

In the embodiment of FIGS. 1-8, the flange 42 has an annular recess 43 formed on the proximal face around the proximal end of the sleeve 32 to receive and capture the distal end of the spring 46. The distal end of the spring 46 can be coupled to the flange 42 and sleeve 32 by a friction fit in the annular recess 43 or can be attached by an adhesive. The collar 44 includes a similar annular recess 45 with a dimension for receiving the proximal end of the spring 46. The proximal end of the spring 46 can be coupled to the collar 44 by a friction fit between the inner surface of the collar and the surface of the syringe barrel or by an adhesive or other attachment mechanism.

The spring 46 slides on the syringe barrel and biases the sleeve to the extended position where the distal end 38 of the sleeve covers at least a portion the of the needle 22. In the extended position, the distal end 38 of the sleeve 32 is at least aligned with the tip of the needle or spaced axially in the distal direction from the tip of the needle. In the extended position, the distal end of the sleeve is able to contact the skin prior or simultaneously with the needle contacting the skin of the patient.

In one embodiment, the flange 42 slides freely on the outer surface of the syringe barrel where the flange 42 and sleeve 32 are retained by the attachment to the distal end of the spring 46. The spring 46 is fixed to the collar 44 so that the attachment of the spring to the flange 42 and sleeve 32 prevent the separation of the sleeve 32 from the syringe barrel. In this embodiment, the spring 46 has an axial length so that the flange 42 does not extend past the distal end of the syringe barrel so that the sleeve can slide freely on the syringe barrel.

Figure 4:
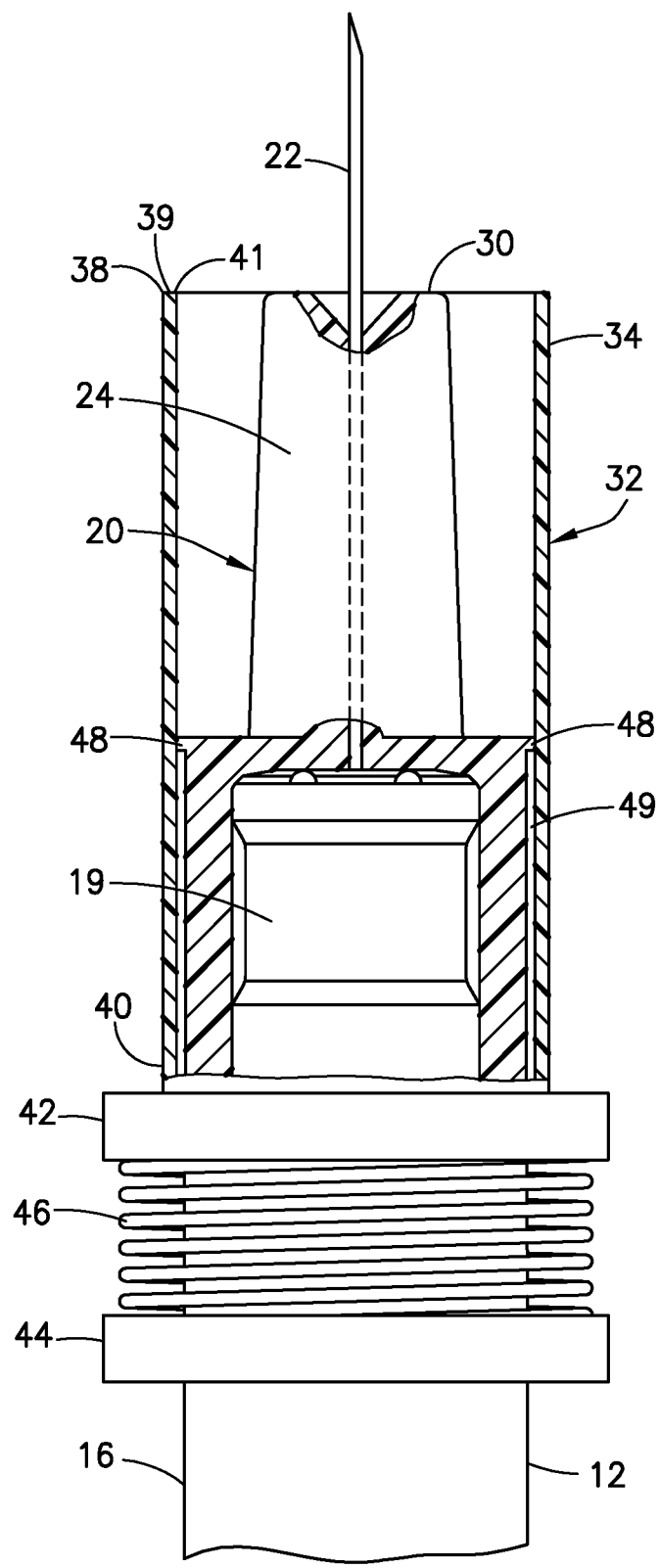
FIG. 4 is an enlarge view of the syringe tip showing the sleeve in the retracted position.
Figure 5:
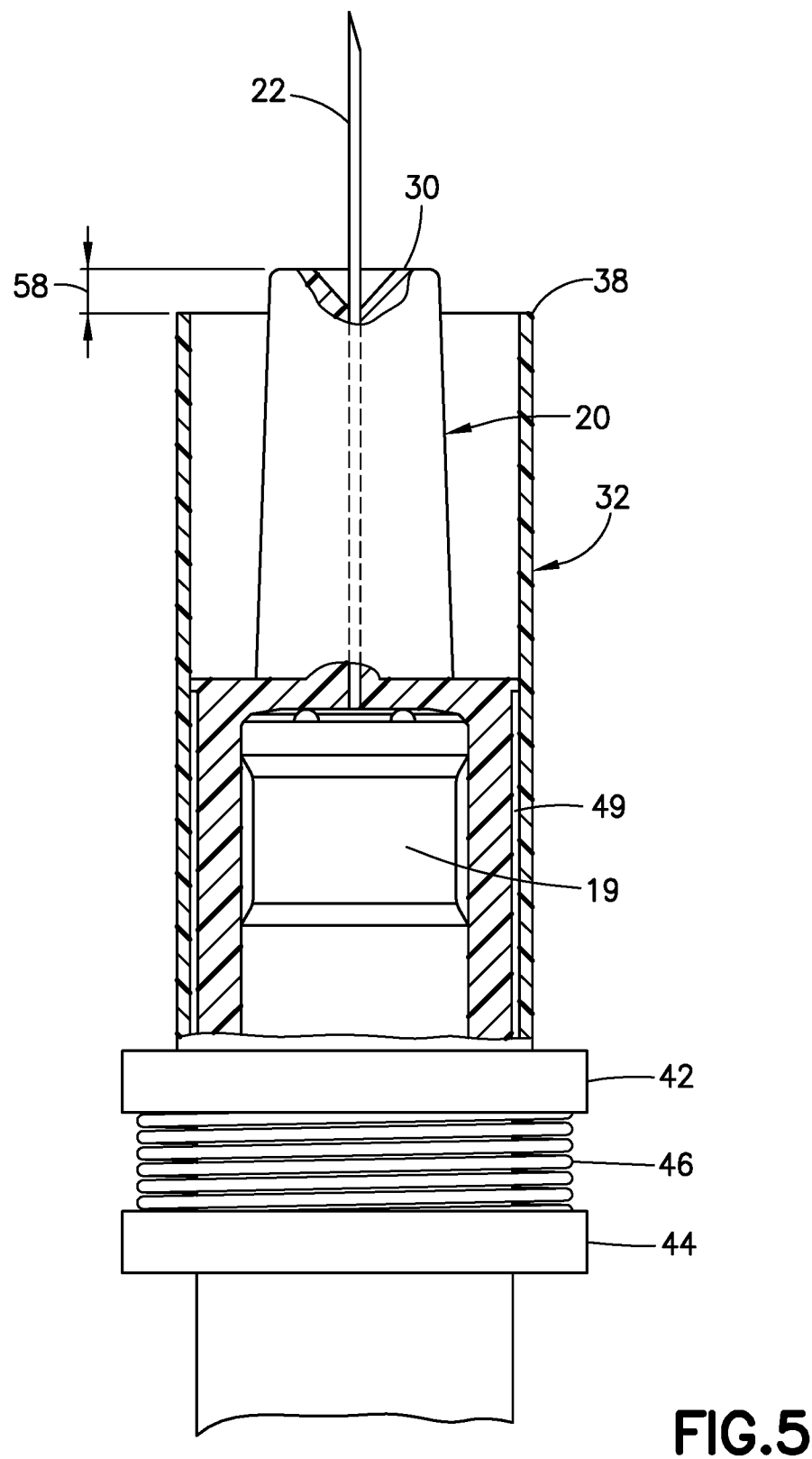
FIG. 5 is an enlarged view of the syringe tip showing the tip of the syringe extending past the end of the sleeve.

In one embodiment, a flange 48 extending radially outward from the syringe barrel forms a longitudinally extending track 49 where the flange functions as a stop member on the outer surface of the syringe barrel at the distal end as shown in FIG. 4 to limit the outward sliding of the flange 42 and sleeve 32 in the distal direction and to retain the sleeve on the syringe barrel. The distal face of the flange 42 can contact the flange 48. In other embodiments, the flange 42 on the sleeve or the sleeve 32 can have an inwardly extending portion 51 that engages the flange 48 to retain the sleeve on the syringe barrel and slides in the rack 49. The inwardly extending portion of the flange 42 can be spaced from the distal face to form an annular recess 47. Alternatively, the flange 42 can have an inwardly extending detent for engaging the flange 48 on the syringe barrel. In other embodiments, the flange can have an inwardly projecting detent that slides in a slot formed on the outer surface of the syringe barrel.

The sleeve 32 is biased by the spring 46 in a manner where the sleeve can be retracted when the needle is inserted into the patient and the sleeve contacts the surface of the skin during the penetration of the needle. The sleeve can be retracted to a position where the distal end face 30 of the hub 20 can project from the distal end of the sleeve and is able to contact the surface of the skin to limit the depth of penetration of the needle.

Figure 7:
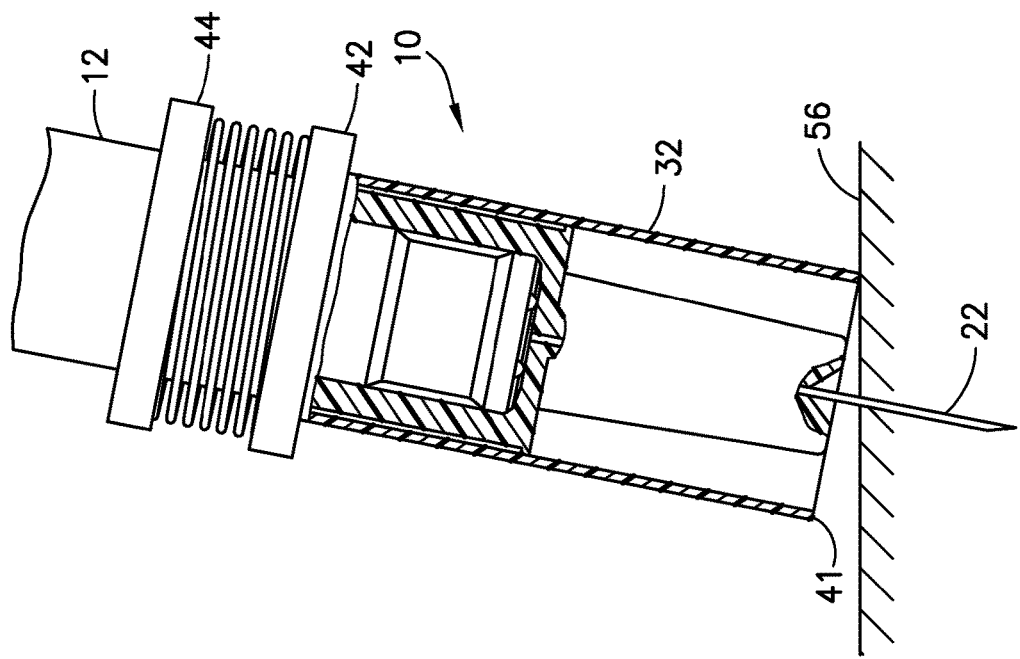
FIG. 7 is a side view of the syringe assembly showing the needle penetrating the skin and the sleeve retracting onto the syringe barrel.
Figure 6:
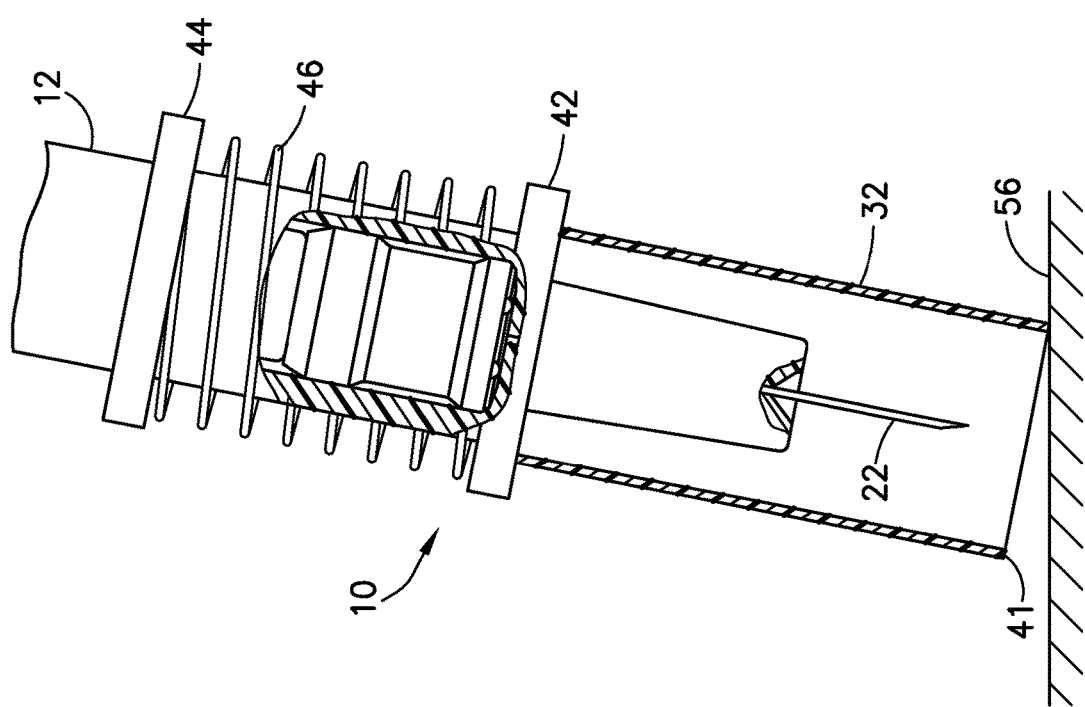
FIG. 6 is a side view of the syringe assembly during insertion of the needle into a patient.
Figure 8:
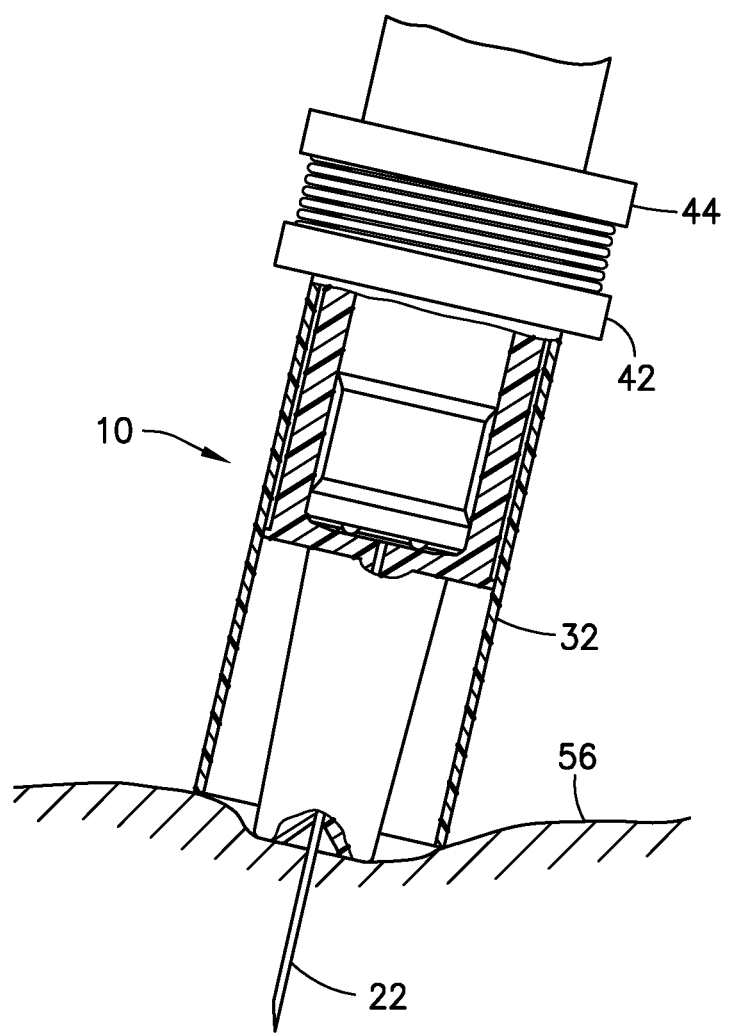
FIG. 8 is a side view of the syringe assembly showing the tip of the syringe contacting the skin of the patient during the injection of the medication into the patient.

The method of use of the syringe assembly is shown in FIGS. 6-8. During use by the patient for self-injection of insulin, the needle is not necessary perpendicular to the surface of the skin so that the needle penetrates at an inclined angle relative to the surface of the skin. The inclined angle can result in a lateral force against the small diameter needle so the needle can bend and result in discomfort to the patient and result in improper depth of penetration. The syringe assembly 10 can be positioned at an inclined angle with respect to the surface of the skin 56 as shown in FIG. 6. In the position shown in FIG. 6, the distal end of the sleeve 32 contacts the surface of the skin before the tip of the needle engages the skin.

The distal face 39 of the distal end 38 of the sleeve has a slip-resistant surface 41 providing a roughness, tacky, or other non-slip surface to inhibit sliding movement of the distal end of the sleeve on the surface of the skin 56. The surface roughness on the distal end of the sleeve 32 can be, for example, a textured surface, a coating, adhesive, tacky material, or other a surface having a coefficient of friction to prevent or inhibit the end of the distal end of the sleeve from sliding on the skin. The textured surface can be formed by a polymer coating, dimples, scoring or the like. In one embodiment, the slip resistant surface is formed by a polymeric coating of an elastomeric material, rubber, or other pliable and/or tacky material that provides a coefficient of friction to inhibit sliding of the sleeve on the surface of the skin when an injection force is applied to the device at an inclined angle relative to the surface of the skin.

FIG. 7 shows the needle penetrating the skin 56 of the patient while the distal end of the sleeve engages the skin to resist the lateral sliding movement on the skin by the insertion force. The slip resistant distal face of the skin contact surface of the sleeve 32 contacts the skin during the insertion to inhibit or reduce the sliding of the needle and sleeve caused by a lateral force of the needle against the skin to inhibit bending of the needle. By the complete insertion of the needle into the skin as shown in FIG. 8, the distal face of the hub projects from the distal end of the sleeve to make complete contact with the skin. The distal face 30 of the hub contacts the skin and has a configuration and dimension to limit or control the depth of penetration of the needle. The distal face 30 extends from the distal end of the sleeve 32 a distance where the distal end of the sleeve and the distal end of the hub form a skin contact surface to control the deformation of the skin by a normal insertion force and to control the depth of penetration. The distal end 38 of the sleeve 32 contacts the skin to limit the depth of deformation by the distal face of the hub by distributing the insertion force and pressure over a defined surface area. The sleeve 32 in the retracted position is limited by the collar 44 on the syringe barrel so that the distal face 39 of the sleeve firmly contacts the skin during the needle insertion. By the contact of the sleeve with the skin, the distal face of the hub is prevented from forming a deep depression in the skin and a needle penetrating deeper than intended.

The distal face of the hub projects from the distal end of the sleeve a predetermined distance when the sleeve is in the retracted position. The distal face of the hub can project from the distal end of the sleeve a distance of about 1 to 7 mm and typically about 2-3 mm indicated by arrow 58 in FIG. 5 to provide the controlled deformation of the surface of the skin by skin contact with the distal face of the needle hub 20 and the distal face 39 of the sleeve 32. The annular space or gap between the needle hub and the inner edge of the distal end of the sleeve has radial width so that the skin is able to deform and stretch into the annular space in a controlled manner to tighten the surface of the skin and limit the depth of the indentation formed by the distal end of the needle hub. The spring 46 biases the sleeve to the extended position when the needle is removed from the skin. In the embodiment shown, the sleeve slide freely on the syringe barrel and does not have a locking or latching mechanism that will retain the sleeve in the extended position after use.

Figure 9:
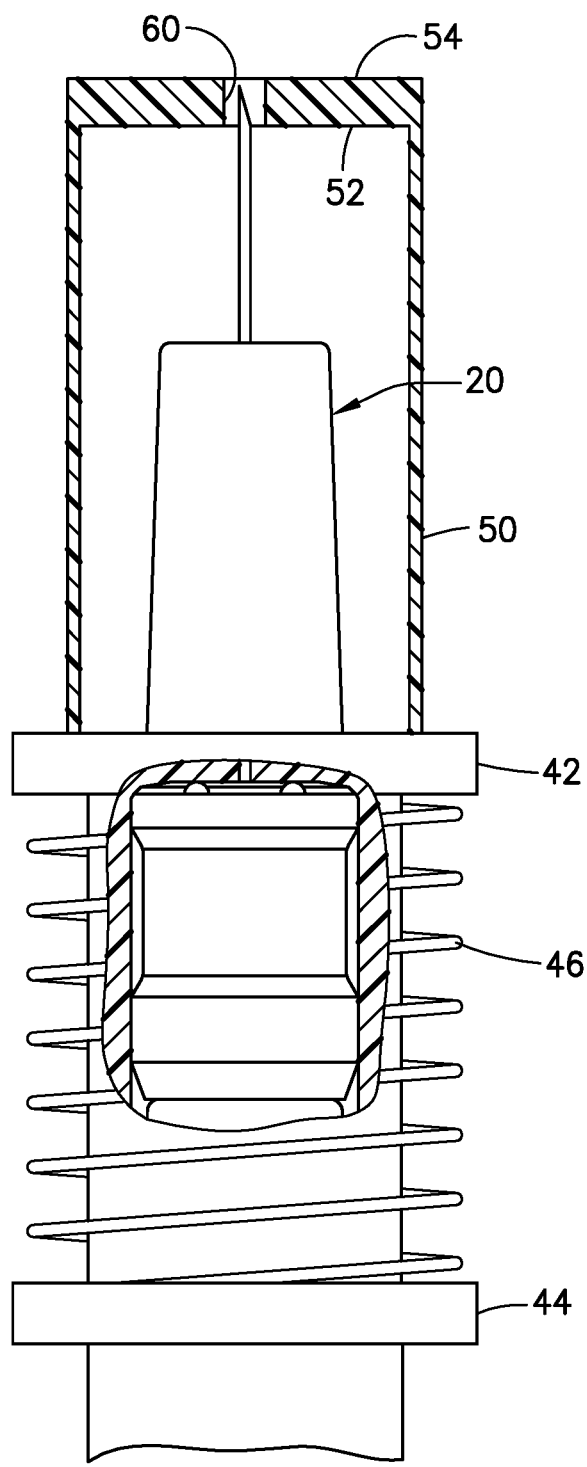
FIG. 9 is a partial cross-sectional view of the syringe assembly in another embodiment.
Figure 10:
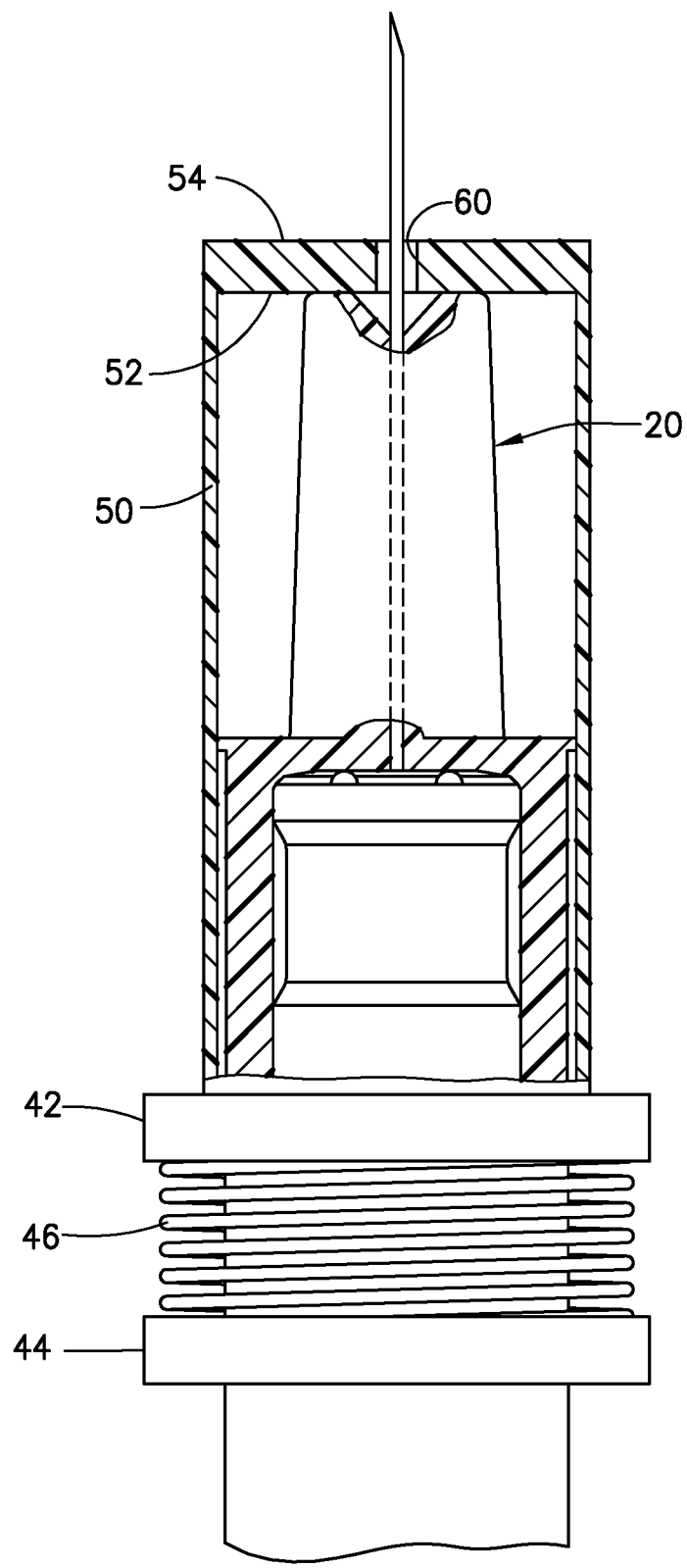
FIG. 10 is a partial cross-sectional view of the syringe assembly FIG. 9 showing the sleeve in the retracted position.

An alternative embodiment of the sleeve is shown in FIGS. 9 and 10. In this embodiment, the sleeve 50 includes an end wall 52 with an opening 60 to allow the needle to extend from the sleeve when the sleeve is in the retracted position shown in FIG. 10. In the embodiment shown, the opening 60 has a dimension smaller than the outer dimension of the needle hub 20. The opening 60 has an inner dimension sufficient to allow the needle to pass through without interference while providing a minimal clearance to stabilize the needle and inhibit bending of the needle during insertion. The structure of the syringe assembly, operating spring, and members for retaining the spring are similar to the previous embodiment. The end wall 52 has a distal face 54 forming a skin contact surface during use. The end wall 52 is configured to contact the distal end of the needle hub to limit the sliding movement of the sleeve in the proximal direction with respect to the syringe and hub. In the retracted position shown in FIG. 10, the inner surface of the end wall 52 engages the distal end of the hub. The end wall 52 can have a textured surface or slip resistant surface to inhibit sliding on the skin of the patient as in the previous embodiment. The method of using the syringe assembly of FIG. 9 is substantially the same as in the previous embodiment. The distal face 54 of the sleeve 50 forms the skin contact surface to control the depth of penetration of the needle. As in the previous embodiment, the dimension of the distal face 54 is selected to provide a contact surface for controlling and limiting the depth of penetration of the needle.

Figure 12:
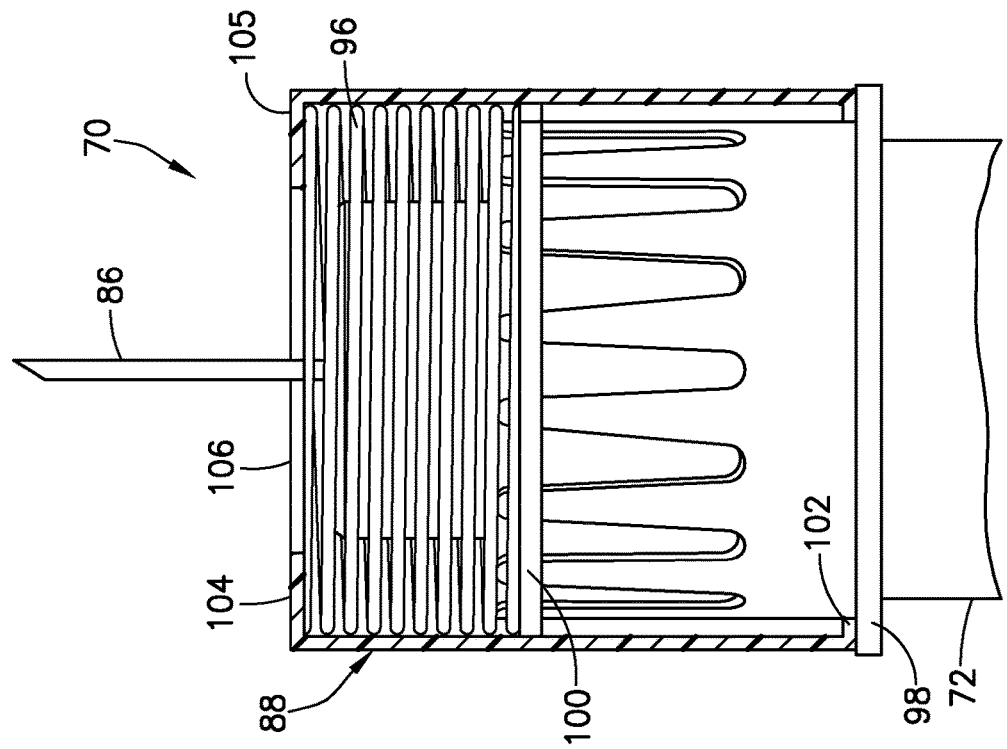
FIG. 12 is a side view of the pen needle showing the sleeve in the retracted position.
Figure 11:
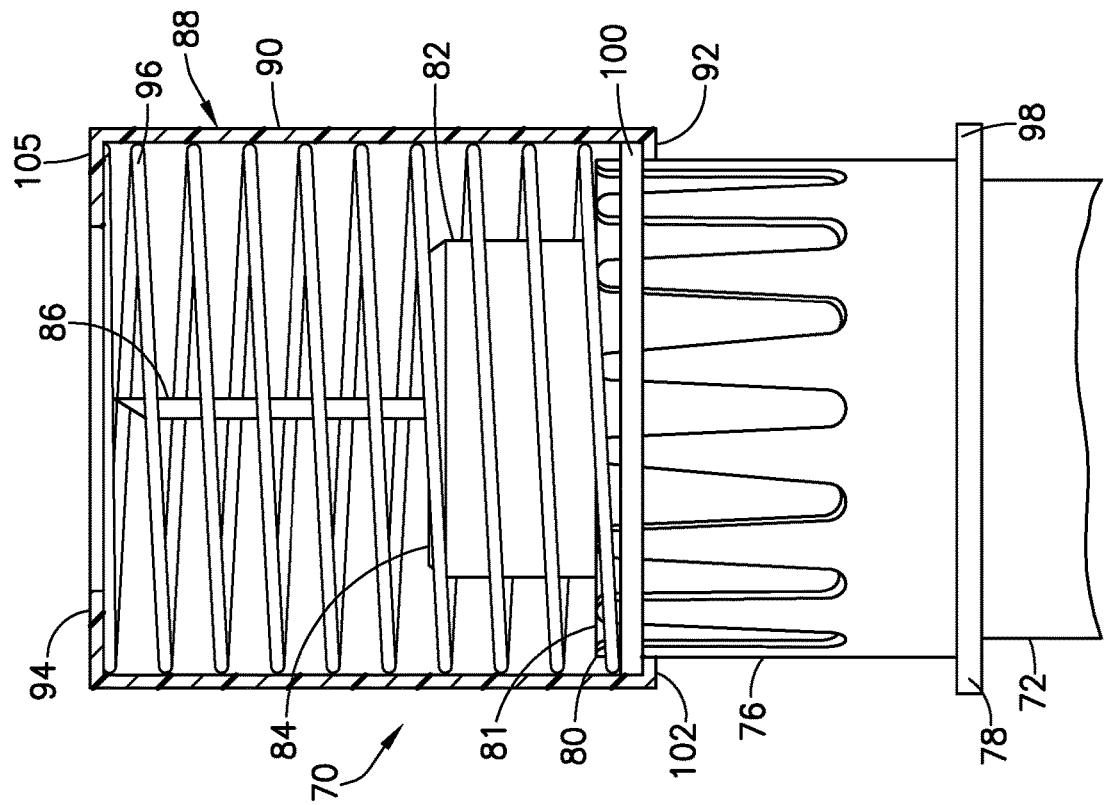
FIG. 11 is a side view of a pen needle in another embodiment showing the sleeve in the extended position.

Referring to FIGS. 11 and 12 another embodiment of the injection assembly is shown where a pen needle 70 is connected to a pen needle delivery device 72. The pen needle delivery device 72 is a commonly used pen needle delivery device for use in injecting insulin to a patient by controlled dose. The pen needle delivery device includes a cartridge containing a medication, a plunger and a dose control knob as known in the art. The pen needle delivery device is configured for delivering a selected dosage of the medication to the patient by the pen needle 70.

The pen needle 70 has a substantially cylindrical body 74 with a side wall 76 having an open proximal end 78 for coupling to the delivery device by internal threads on the inner surface of the side wall 76. A distal end 80 of the body 74 includes an end wall 81 with a distal face and a tower 82 extending axially from the body in the distal direction. The tower 82 has an axially facing end surface 84 and a needle 86 extending axially from the axial end surface 84. The end surface 84 defines a skin contact surface for contacting the skin and limiting a depth of penetration of the needle into the skin of the patient during the injection of the medication.

A sleeve 88 is coupled to the body 74 for sliding between an extended position shown in FIG. 11 and a retracted position shown in FIG. 12. The sleeve 88 has a substantially cylindrical side wall 90 with an open proximal end 92 and an open distal end 94 with an inner dimension to slide over the side wall 76 of the body. A spring 96 is provided between the body 74 and the sleeve 88 to bias the sleeve in the distal direction with respect to the pen needle. In the embodiment shown, the spring 96 is a coil spring surrounding the inner surface of the side wall 90. The spring 96 can extend between the distal end of the sleeve 88 and the end wall 81.

As shown in FIG. 11, the body 74 of the pen needle has an outwardly extending member 98 at the proximal end 76 for limiting the length of travel of the sleeve 88 in the proximal direction. A member 100 extends radially outward from the distal end of the side wall 76 at the distal end 80 of the body 74 to limit the length of travel of the sleeve in the distal direction. The outwardly extending member 98 and the outwardly extending member 100 are shown as radial flanges although other shapes, dimensions and configurations can be used that are suitable to limit movement of the sleeve. In the embodiment shown, the member 98 and member 100 are integrally formed with the side wall 76 at the open proximal end of the side wall. In other embodiments, the member 98 and the member 100 can be a separate ring-shaped member fixed to the side wall 76 by a friction fit, adhesive or welding. The sleeve 88 has an inwardly extending member shown as a flange 102 at the proximal end of the sleeve where the flange 102 is received between the flange 98 and flange 100 for sliding movement and limiting the travel of the sleeve relative to the body 74 of the pen needle. The flange 102 has an inner diameter corresponding to the outer diameter of the side wall 76. An inwardly extending member such as a flange 104 is provided at the distal end of the sleeve for capturing the spring 96. The spring 96 extends between the distal face of the member 100 at the end wall 81 of the body 74 and the inner face of the flange 104 to bias the sleeve 88 outwardly in the distal direction with respect to the pen needle.

The flange 104 in the distal end of the sleeve has a dimension to retain the spring 96 and is sufficiently wide to allow the axial face 84 to project through the opening to enable contact of the axial face 84 of the body with the skin when the needle is inserted into the skin. The sleeve 88 is biased to the extended position shown in FIG. 11 where the sleeve extends at least equal to the length of the needle 86 and typically past the tip of the needle. During insertion of the needle into the skin of the patient, the distal end of the sleeve contacts the skin of the patient before the needle in a manner similar to the previous embodiment. A slip resistant surface 105 of the distal end of the sleeve inhibits sliding of the sleeve on the skin. Continued insertion of the needle causes the sleeve to retract to the position shown in FIG. 12 where the needle 86 projects from the distal end of the sleeve 88. The insertion force contacts the surface of the skin with the distal end of the sleeve and the axial face 84 of the tower 82 to control the shape and configuration of the indentation and the depth of penetration of the needle by controlling the deformation of the skin surface. The tower 82 can have an axial length so that the axial face of the tower 82 can be recessed, flush with, or project above the end wall 104 of the sleeve when the sleeve is retracted. The proximal movement of the sleeve is limited by the spring in the compressed state and the flange 102 contacting the flange 88.

Figure 14:
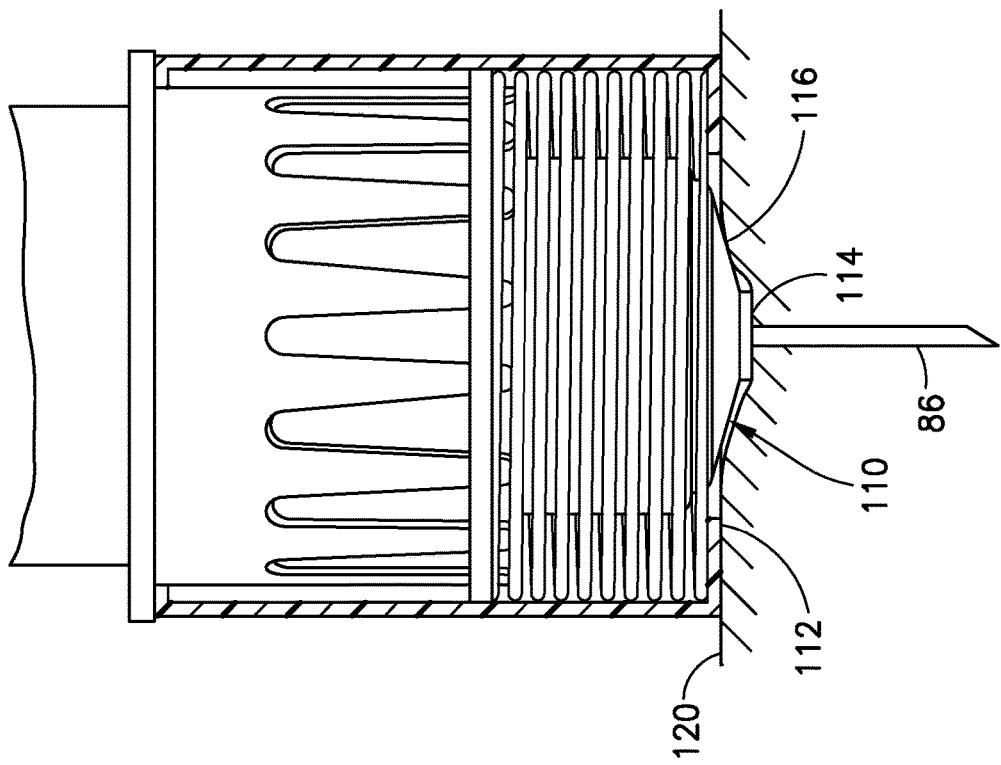
FIG. 14 is a side view of the pen needle of FIG. 13 showing the sleeve in the retracted position.
Figure 13:
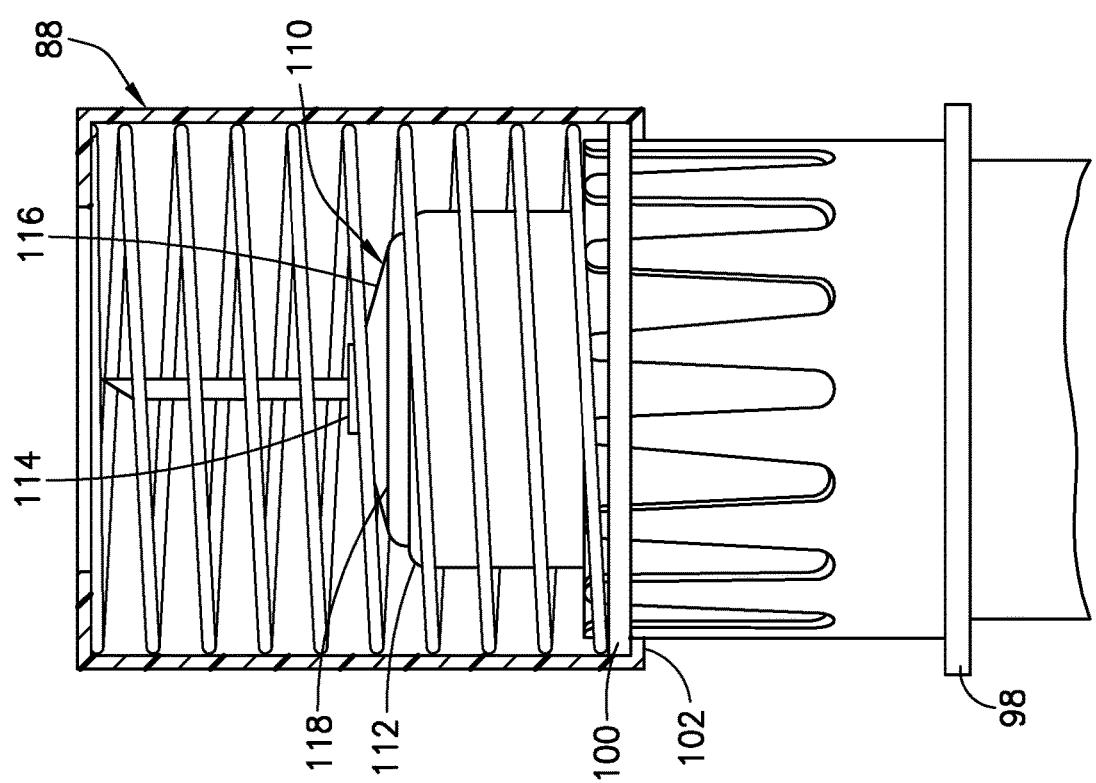
FIG. 13 is a side view of the pen needle in another embodiment showing the sleeve in the extended position.

FIGS. 13 and 14 show a further embodiment of the pen needle that is substantially the same as the embodiment of FIGS. 11 and 12 except for the skin contact surface of the pen needle. The body 74 of the pen needle, the sleeve 88, and spring 96 are substantially the same and are identified by the same reference numbers.

In the embodiment of FIGS. 13 and 14 the tower 82 of the body extends axially in the distal direction. The axial end face 100 of the tower 82 is formed with a convex distal surface to define the skin contact surface during the injection of the medication to the patient. The convex surface extends between the outer perimeter 102 of the tower and a center portion 114 around the needle 86. The center portion 112 around the needle defines the outermost distal end of the convex surface 110. A conical shaped portion 116 extends from the perimeter 112 of the tower toward the center portion 114. The center portion 114 projects from the conical shaped portion 116. The center portion 114 in one embodiment can be a ring shaped projection extending in the distal direction from the conical portion 116. The outer peripheral edge can also be formed with a ring shaped projection 118 extending from the conical portion 116 to define an annular recess with the bottom surface of the recess forming the conical surface of the conical shaped portion 116.

As shown in FIG. 14, the sleeve 88 is retracted by the insertion force of the pen needle against the surface of the skin 120 of the patient. In the retracted position, the sleeve 88 is retracted to a position where the distal end of the tower protrudes from the distal end of the sleeve. The center portion 114 of the distal face contacts the surface of the skin during insertion of the needle 86 into the patient where the center portion forms an indentation in the skin 120 by the resiliency of the skin. The penetrating force then causes the conical shaped portion 116 to contact the skin to distribute the pressure and control the deformation of the skin and control the depth of indentation by the center portion and thereby control the depth of penetration by the needle. After the injection, the needle is withdrawn from the patient and the sleeve returns to the original position of FIG. 13 to cover the needle.

Figure 15:
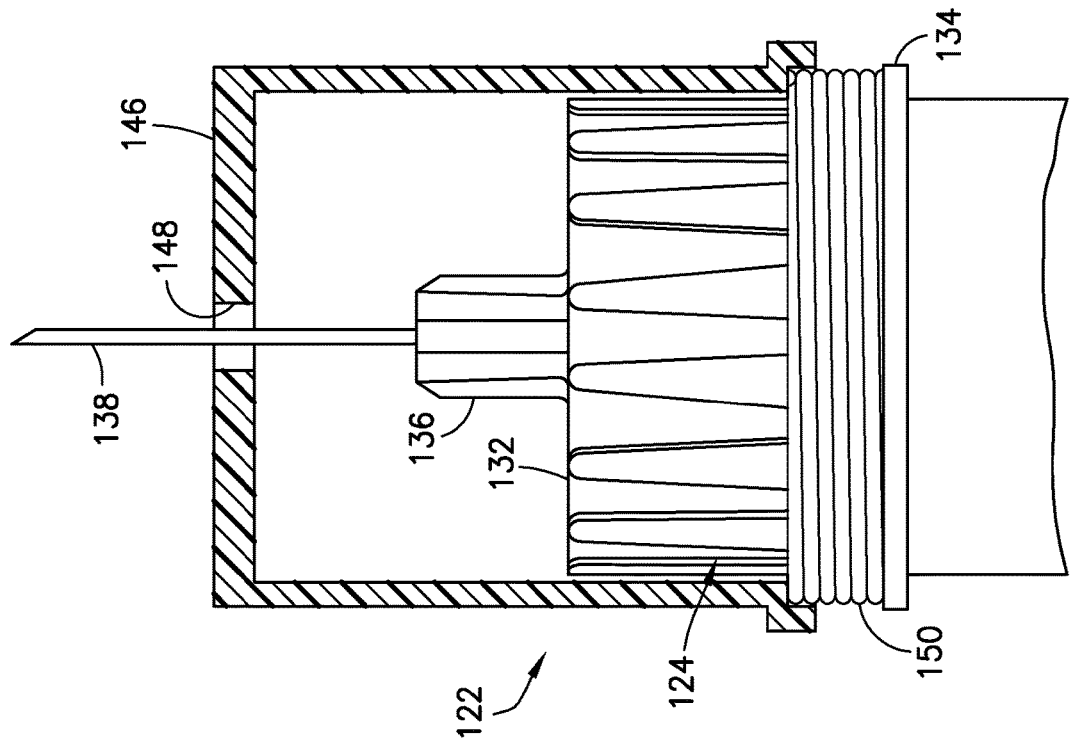
FIG. 15 is a side view of the pen needle in a further embodiment showing the sleeve in the extended position.
Figure 16:
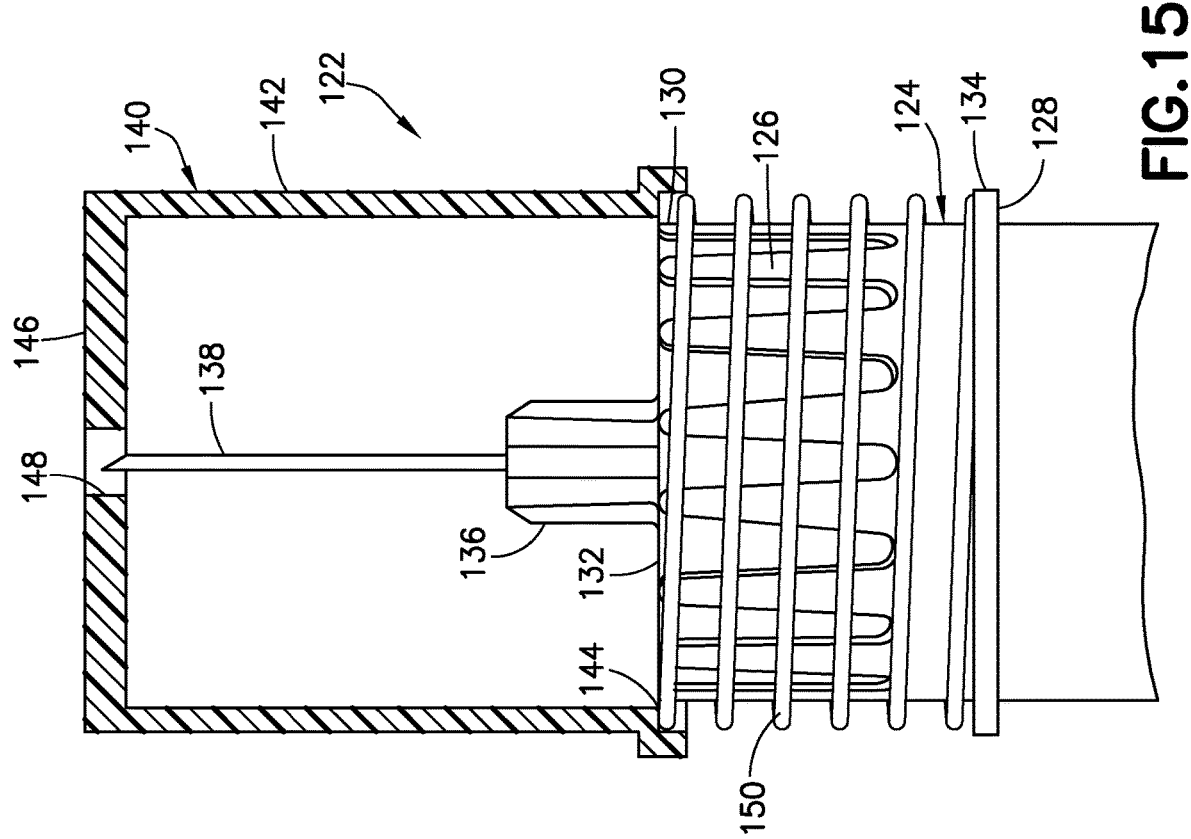
FIG. 16 is a side view of the pen needle of FIG. 15 showing the sleeve in the retracted position.

FIGS. 15 and 16 show another embodiment of the pen needle 122 of the invention. The pen needle includes a body 124 having a side wall 126 with an open proximal end 128 and a distal end 130. An end wall is provided at the distal end of the body 124 to form a closed distal end. An outwardly extending flange 134 projects from the proximal end of the side wall 126. A tower 136 projects from the end wall for supporting a needle 138 for injecting the medication to the patient.

A sleeve 140 is coupled to the body 140 of the pen needle for sliding movement between an extended position shown in FIG. 15 and a retracted position shown in FIG. 16. The sleeve has a substantially cylindrical side wall 142 with an open proximal end 144 with an inner dimension to receive and slide on the body of the pen needle. The sleeve has a distal end with an end wall 146. An opening 148 is formed in the end wall and has a dimension to allow the needle 138 to pass through when the sleeve is moved to the retracted position. In the embodiment shown, the tower of the body of the pen needle does not extend through the opening in the end wall.

Figure 17:
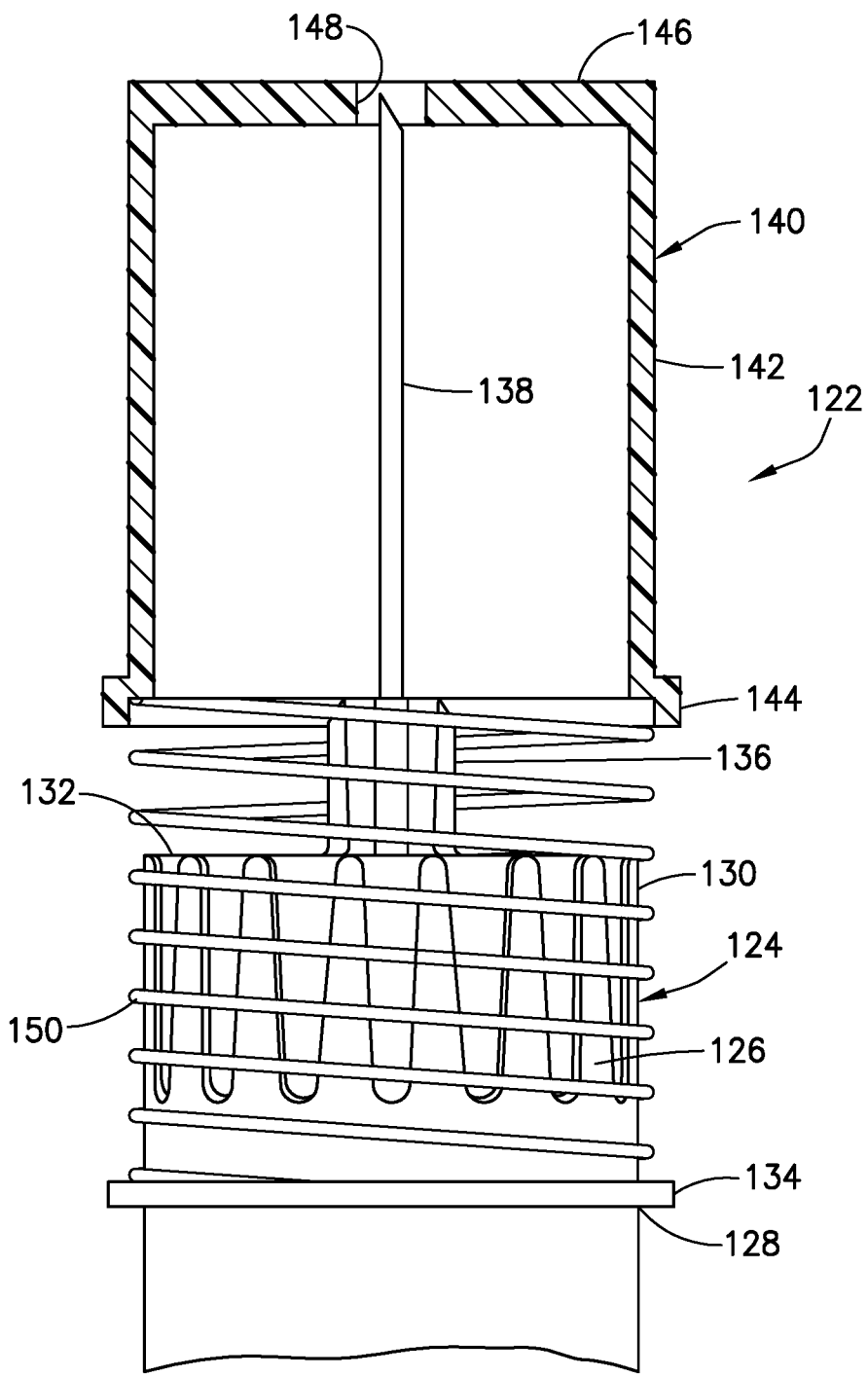
FIG. 17 is a side view of another embodiment of the pen needle.

A spring 150 is provided on the outer surface of the side wall 142 of the body and extends between the flange 134 at the proximal end of the side wall and the proximal end 144 of the sleeve 140 for biasing the sleeve to the extended position. As shown, the side wall 142 has an outwardly extending flange forming an annular recess for capturing and retaining the spring 150. During use, the pen needle is positioned against the surface of the skin of the patient and an insertion force is applied. The sleeve engages the skin to resist sliding or lateral movement of the pen needle on the surface of the skin during the insertion of the needle. As in the previous embodiment, the end wall can have a slip resistant surface to resist sliding of the sleeve against the surface of the skin during insertion of the needle. The sleeve slides to the retracted position as the needle is inserted into the patient to the position shown in FIG. 16. The distal face of the end wall of the sleeve forms a skin contact surface to control the deformation of the skin and limit the depth of penetration of the needle. In another embodiment shown in FIG. 17, the distal end of the body 124 does not have a stop or retaining member so that the sleeve 140 is retained on the body 124 by the spring fixed to an outwardly extending flange forming an annular recess for capturing and retaining the spring 150.

The foregoing embodiments and advantages are exemplary and are not intended to be construed as limiting the scope of the invention. The description of alternative embodiments are intended to be illustrative, and not to limit the scope of the present invention. Various modifications, alternatives, and variations will be apparent to those skilled in the art, and are intended to fall within the scope of the invention. It is particularly noted that the features of different embodiments and claims may be combined with each other as long as they do not contradict each other. Accordingly all such modifications are intended to be included within the scope of this invention as defined in the appended claims and their equivalents.

The invention claimed is:

1. An injection assembly comprising: a body for connecting to a fluid supply, said body having a proximal end and a distal end, said distal end of said body having a skin contact surface, said body having a side wall with an outwardly projecting member spaced from said distal end; a needle extending from said distal end of said body, said needle having an axial length, a proximal end coupled to said body, and a distal end spaced from said skin contact surface of said body; a movable sleeve on said side wall of said body for sliding movement between an extended position and a retracted position with respect said body in an axial direction, said sleeve having a proximal end connected to said body and a distal end with a skin contact surface, and a spring member surrounding said side wall of said body and extending between and directly contacting said outwardly projecting member and said sleeve, said sleeve being biased in the distal direction where said distal end of said sleeve is oriented to cover said distal end of said needle, said sleeve being slideable to the retracted position where said distal end of said body is exposed to contact the skin of a patient.

2. The injection assembly of claim 1, wherein said injection assembly is a syringe assembly having a syringe barrel with a distal end, said syringe assembly including a needle hub at said distal end of said syringe barrel and having a distal end of said needle hub forming said skin contact surface of said body, and said sleeve coupled to said syringe barrel for sliding relative to said syringe barrel and needle hub.

3. The injection assembly of claim 2, where distal end of said sleeve forming said skin contact surface has an end wall with a slip resistant surface, said end wall having an opening with a dimension complementing said skin contact surface of said needle hub whereby said skin contact surface of said body projects distally from said end wall of said sleeve when said sleeve is in the retracted position.

4. The injection assembly of claim 2, wherein said syringe barrel has a collar fixed to an outer surface of said syringe barrel, said proximal end of said sleeve has an inwardly extending flange, and where said spring extends between and contacts said collar and said flange to bias said sleeve in the distal direction.

5. The injection assembly of claim 4, wherein said spring is a coil spring surrounding an outer surface of said syringe barrel and has a proximal end engaging said collar on said syringe barrel and a distal end engaging a proximal end of said sleeve.

6. The injection assembly of claim 5, wherein said proximal end of said sleeve includes an outwardly extending flange and where said distal end of said spring directly engages a proximal side of said flange.

7. The injection assembly of claim 6, wherein said flange on said sleeve is a ring-shaped member coupled to an outer surface of said sleeve.

8. The injection assembly of claim 6, wherein said proximal side of said flange on said sleeve comprises an annular recess receiving and coupling to said distal end of said spring, and said collar on said syringe barrel has a distal side with an annular recess receiving and coupling to said proximal end of said spring.

9. The injection assembly of claim 1, wherein said injection assembly is a pen needle, said proximal end of said body configured for coupling to a pen needle delivery device, and said sleeve is coupled to said side wall of said body for sliding on said side wall between said extended position and said retracted position.

10. An injection assembly comprising: a body for connecting to a fluid supply, said body having a proximal end and a distal end, said distal end of said body having a skin contact surface, said body having a side wall with an outwardly projecting member spaced from said distal end; a needle extending from said distal end of said body, said needle having an axial length, a proximal end coupled to said body, and a distal end spaced from said skin contact surface of said body; a movable sleeve on said side wall of said body for sliding movement between an extended position and a retracted position with respect said body in an axial direction, said sleeve having a proximal end connected to said body and a distal end with a skin contact surface, and a spring member around said side wall of said body and extending between and contacting said outwardly projecting member and said sleeve, said sleeve being biased in the distal direction where said distal end of said sleeve is oriented to cover said distal end of said needle, said sleeve being slideable to the retracted position where said distal end of said body is exposed to contact the skin of a patient; wherein said injection assembly is a pen needle, said proximal end of said body configured for coupling to a pen needle delivery device, and said sleeve is coupled to said side wall of said body for sliding on said side wall between said extended position and said retracted position and wherein said body of said pen needle comprises said skin contact surface, and where said skin contact surface has a convex shape, and where said distal end of said sleeve has an inner dimension complementing said convex skin contact surface whereby said convex skin contact surface of said pen needle projects from said open end of said sleeve to contact the skin of the patient when said sleeve is in the retracted position.

11. The injection assembly of claim 10, wherein said distal end of said sleeve has an axially facing skin contact surface with a slip resistant surface to inhibit sliding of said sleeve relative to the surface of the skin of the patient.

12. The injection assembly of claim 11, wherein said sleeve includes a sleeve side wall having a first flange at said distal end of said sleeve side wall, said sleeve side wall has a second flange at a proximal end of said sleeve side wall, said spring having a proximal end coupled to said first flange and a distal end coupled to said second flange to bias said sleeve in the distal direction relative to the body.

13. The injection assembly of claim 12, wherein said side wall of said sleeve has an inwardly extending flange, said flange received between said first flange and said second flange to limit sliding movement of said sleeve with respect to said side wall.

* * * * *